United States Patent [19]

Ackerson et al.

[11] Patent Number: 5,017,215

[45] Date of Patent: May 21, 1991

[54] HERBICIDES FOR WEED CONTROL IN RICE

[75] Inventors: Robert C. Ackerson, Newark, Del.; Takeshi Yuyama, Inashiki, Japan

[73] Assignee: E. I. Du Pont De Nemours and Company, Wilmington, Del.

[21] Appl. No.: 437,802

[22] Filed: Nov. 17, 1989

Related U.S. Application Data

[63] Continuation-in-part of Ser. No. 407,066, Sep. 14, 1989, abandoned, which is a continuation-in-part of Ser. No. 288,511, Dec. 22, 1988, abandoned, which is a continuation-in-part of Ser. No. 219,270, Jul. 15, 1988, abandoned, which is a continuation-in-part of Ser. No. 194,549, May 16, 1988, abandoned, which is a continuation-in-part of Ser. No. 157,548, Feb. 12, 1988, abandoned, which is a continuation-in-part of Ser. No. 82,697, Aug. 7, 1987, abandoned.

[51] Int. Cl.$^5$ ............................................. A01N 43/64
[52] U.S. Cl. ............................................. 71/93; 71/92
[58] Field of Search ............................................. 71/93

[56] References Cited

U.S. PATENT DOCUMENTS

| | | | |
|---|---|---|---|
| 3,382,280 | 5/1968 | Huffman | 260/562 |
| 3,736,122 | 5/1973 | Tung et al. | 71/103 |
| 3,816,092 | 6/1974 | Wilson et al. | 71/118 |
| 4,383,113 | 5/1983 | Levitt | 544/211 |
| 4,394,506 | 7/1983 | Levitt | 544/321 |
| 4,479,821 | 10/1984 | Meyer et al. | 71/93 |
| 4,601,746 | 7/1986 | Westermann et al. | 71/92 |
| 4,645,527 | 2/1987 | Amuti et al. | 71/90 |

FOREIGN PATENT DOCUMENTS

| | | |
|---|---|---|
| 158600 | 4/1984 | European Pat. Off. |
| 82306 | 5/1984 | Japan |
| 82307 | 5/1984 | Japan |
| 112703 | 6/1985 | Japan |
| 112003 | 5/1986 | Japan |

OTHER PUBLICATIONS

Klingmann et al., "Weed Science: Principles and Practices", pp. 305–306 (1982).

Takeda et al., Zasso Kenkyu (Weed Research, Japan), 31(2), 157–63 (1986).

Takeda et al., Zasso Kenkyu (Weed Research, Japan), 30(4), 278–83 (1985).

*Primary Examiner*—Richard L. Raymond
*Assistant Examiner*—John D. Pak

[57] ABSTRACT

This invention relates to a composition comprising a mixture of herbicidal compounds and a method for controlling the growth of undesired vegetation in upland cereal and rice crops by applying to the crop after transplantation or emergence an effective amount of certain sulfonylurea herbicides, alone or the above composition comprising a mixture of herbicidal compounds.

1 Claim, No Drawings

HERBICIDES FOR WEED CONTROL IN RICE

RELATED APPLICATIONS

This is a continuation-in-part of U.S. Ser. No. 07/407,066 filed Sept. 14, 1989, now abandoned, which is a continuation-in-part of U.S. Ser. No. 07/288,511, filed Dec. 22, 1988, now abandoned, which is a continuation-in-part of U.S. Ser. No. 07/219,270 filed July 15, 1988, now abandoned, which is a continuation-in-part of U.S. Ser. No. 194,549 filed May 16, 1988, now abandoned, which is a continuation-in-part of U.S. Ser. No. 157,548 filed Feb. 12, 1988, now abandoned, which is a continuation-in-part of U.S. Ser. No. 082,697 filed Aug. 7, 1987, now abandoned.

BACKGROUND OF THE INVENTION

This invention relates to novel compositions comprising mixtures of two herbicides and to a method of controlling undesired vegetation in the growth of upland cereal and rice crops by the application of an effective amount of one of the herbicides that comprise the mixture, alone or the composition comprising the mixture.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. There is especially a need for finding compounds that selectively control the growth of undesired vegetation in growing rice. Rice is a staple crop for millions of people of the world whose diet depends on its availability. There are many products commercially available for such purposes, but the search continues for products which are more effective, less costly and environmentally safe.

The "sulfonylurea" herbicides are an extremely potent class of herbicides discovered within the last few years. A multitude of structural variations exist within this class of herbicides, but they generally consist of a sulfonylurea bridge, —$SO_2NHCONH$—, linking two aromatic or heteroaromatic rings.

Rice and upland cereals such as wheat, barley, oats etc. satisfy the food need of a large portion of the world's population. The continued population increase and concomitant food shortage increase the need for improvements in the production of such crops. Improving the efficiency of producing such crops by controlling undesirable weeds through the application of herbicides is continually being sought. Along with this improvement the application of herbicides to crops such as rice and wheat without injury thereto is also being sought.

The compound N-(3,4-dichlorophenyl) propionamide (propanil) has been found very effective for controlling weeds in rice crops. U.S. Pat. No. 3,382,280 discloses herbicidal propanil.

U.S. Pat. No. 4,394,506 discloses compounds within the scope of Formula I of the present invention.

U.S. Pat. No. 4,383,113 also discloses compounds within the scope of Formula I of the present invention.

U.S. Pat. No. 4,645,527 discloses the use of certain sulfonamides to protect cereal crops from injury by compounds within the scope of Formula I of the present invention where X is $CH_3$, Y is $OCH_3$ and Z is N.

U.S. Pat. No. 3,816,092 discloses a method for applying propanil to obtain a herbicidal effect.

There is, however, no disclosure in any of the above references of the use of the compounds they describe for control of vegetation with safety to rice or in the combination disclosed herein.

SUMMARY OF THE INVENTION

This invention relates to compositions comprising mixtures of compounds of

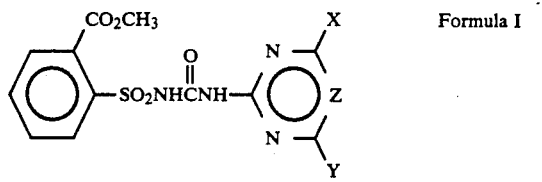

Formula I wherein
X is $CH_3$ or $OCH_3$;
Y is $OCH_3$; and
Z is N or CH,
provided that when Z is CH then X is $OCH_3$ and when Z is N then X is $CH_3$, with compounds selected from 2,4-dichlorophenoxyacetic acid, bensulfuron methyl, thiobencarb, dimepiperate, esprocarb, dymron and propanil.

The preferred mixtures of the invention are the compounds of Formula I wherein Z is N, X is $CH_3$ and Y is $OCH_3$ (metsulfuron methyl) with bensulfuron methyl or propanil.

The combination of a herbicidally effective amount of metsulfuron methyl and propanil produces a synergistic effect in the control of weeds, such as nutsedge.

This combination also provides a broad weed spectrum control that includes grasses such as barnyard grass and broadleaves such as cocklebur. The combination of compound I and II controls upland weeds and aquatic weeds. On applications to rice crops said applications can be made to dry seeded, water seeded or transplanted rice. The combination may be applied postemergent after planting the crop but preemergent and/or postemergent to the weeds prior to establishment of permanent flood on rice. That is, the combination may be applied to rice after flooding when the water is removed prior to permanent flooding.

What is meant by upland cereal is oats, wheat, barley, rye and triticale.

The combination of compound I and II permits the usage of lower rates of application with longer residual activity and also easier water management.

This invention also relates to a method for controlling the growth of undesired vegetation in a rice crop and upland cereals by applying to the crop after transplantation or emergence of the rice plants an effective amount of a compound of Formula I, alone or in combination with other herbicides.

The preferred methods of the invention for reasons of either more effective weed control or better crop tolerance are:

1. A method for controlling the growth of undesired vegetation in a rice crop by applying to the crop after transplantation or emergence of the rice plants an effective amount of a compound of Formula I wherein Z is N, X is $CH_3$ and Y is $OCH_3$.

2. A method for controlling the growth of undesired vegetation in a rice crop by applying to the crop after transplantation or emergence of the rice plants an effective amount of a compound of Formula I wherein Z is CH, X and Y are OCH$_3$.

3. A method of Preferred I in admixture with a herbicidally effective amount of 2,4-dichlorophenoxyacetic acid.

4. A method of Preferred 1 in admixture with a herbicidally effective amount of bensulfuron methyl.

5. A method of Preferred 1 in admixture with S-[(4-chlorophenyl)methyl]diethylcarbamothioate (Thiobencarb).

6 A method of Preferred 1 in admixture with S-1-methyl-1-phenylethylpiperidine-1-carbothioate (Dimepiperate).

7. A method of Preferred 1 in admixture with S-benzyl-N-ethyl-N-(1,2-dimethyl)-propylthiol carbamate (Esprocarb).

8. A method of Preferred 1 in admixture with 1-($\alpha$,$\alpha$-dimethylbenzyl)-3-p-tolylurea (Dymron).

9. A method of Preferred 1 in admixture with N-(3,4-dichlorophenyl)propionamide (Propanil).

Undesired vegetation, especially broadleafed weeds, in a rice crop may be controlled by applying to the crop after transplantation or emergence an effective amount of a compound of Formula I.

Compounds of Formula I may be combined with other rice herbicides, such as 2,4-dichlorophenoxyacetic acid, benzsulfuron methyl, S-[(4-chlorophenyl)-methyl]diethylcarbamothioate, S-1-methyl-1-phenylethylpiperidine-1-carbothioate, S-benzyl-N-ethyl-N-(1,2-dimethyl)propylthiol carbamate or 1-($\alpha$,$\alpha$-dimethylbenzyl)-3-p-tolylurea to broaden the spectrum of weed control.

DETAILED DESCRIPTION OF THE INVENTION

The compounds of Formula I are known in the art Their chemical names are:
methyl 2-[[[[(4-methoxy-6-methyl-1,3,5-triazin-2-yl)amino]carbonyl]amino]sulfonyl]benzoate (X is CH$_3$, Y is OCH$_3$ and Z is N.)
methyl 2-[[[[(4,6-dimethoxy-2-pyrimidinyl)amino]carbonyl]amino]sulfonyl]benzoate (X is OCH$_3$, Y is OCH$_3$ and Z is CH.)

In addition, methyl 2-[[[[(4-methoxy-6-methyl-1,3,5-triazin-2-yl)amino]carbonyl]amino]sulfonyl]benzoate is known under the common name of metsulfuron methyl.

The compounds of Formula I wherein X is OCH$_3$, Y is OCH$_3$, and Z is CH and wherein X is CH$_3$, Y is OCH$_3$ and Z is N can be prepared by the processes specifically taught in Examples 1, 3, 4, 5, 6, 12 and 13 of U.S. Pat. Nos. 4,394,506 and 4,383,113.

Propanil and its preparation is disclosed in U.S. Pat. No. 3,382,280. The use of propanil is disclosed in U.S. Pat. No. 3,816,092.

As discussed in the Utility section, the compounds of the instant invention are particularly effective in controlling broadleafed weeds and sedges when combined with 2,4-dichlorophenoxyacetic acid (2,4-D), its agriculturally suitable esters or salts, or with benzsulfuron methyl, or with Thiobencarb, or with Dimepiperate, or with Esprocarb, or with Dymron or with propanil. 2,4-D, its esters and salts are well known in the art of weed control. Some of its more frequently used esters are prepared from 2-propanol, n-butanol, 2-butoxyethanol and 6-methyl-1-heptanol. Some of its more frequently used salts are sodium, diethanolamine, diethylamine, dimethylamine, ethanolamine, methylamine and triethanolamine. Neither the list of esters nor the list of salts is intended to be limiting.

The complete chemical name of benzsulfuron methyl is methyl 2-[[[[(4,6-dimethoxy-2-pyrimidinyl)amino]carbonyl]amino]sulfonyl]methyl]-benzoate. It is sold under the tradename of Londax ® Herbicide by E. I. du Pont de Nemours and Company for weed control in rice. It is specifically disclosed in U.S. Pat. No. 4,420,325 and can be prepared by the general processes described therein.

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 1to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

| | Percent by Weight | | |
|---|---|---|---|
| | Active Ingredient(s) | Diluent(s) | Surfactant(s) |
| Wettable powders | 20–90 | 0–74 | 1–10 |
| Oil Suspensions, Emulsions, Solutions, (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1985. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc, New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

EXAMPLE 1

Wettable Powder

| | |
|---|---|
| 2,4-dichlorophenoxyacetic acid, sodium salt | 60% |
| methyl 2-[[[[(4-methoxy-6-methyl-1,3,5-triazin-2-yl)amino]carbonyl]amino]sulfonyl]benzoate | 1% |
| dodecylphenol polyethylene glycol ether | 2% |
| sodium ligninsulfonate | 4% |
| sodium silicoaluminate | 6% |
| sodium carbonate | 2% |
| montmorillonite (calcined) | 25% |

The ingredients are thoroughly blended. The liquid surfactant is added by spraying upon the solid ingredients in the blender. After grinding in a hammermill to produce particles essentially all below 100 microns, the material is reblended and sifted through a U.S.S. No. 50 sieve (0.3 mm opening) and packaged.

EXAMPLE 2

Wettable Powder

| | |
|---|---|
| methyl 2-[[[[(4-methoxy-6-methyl-1,3,5-triazin-2-yl)amino]carbonyl]amino]sulfonyl]benzoate | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

EXAMPLE 3

Granule

| | |
|---|---|
| wettable powder of Example 2 | 25% |
| gypsum | 64% |
| potassium sulfate | 11% |

The ingredients are blended in a rotating mixer and water sprayed on to accomplish granulation. When most of the material has reached the desired range of 1.0 to 0.42 mm, (U.S.S. #18 to 40 sieves), the granules are removed, dried and screened. Oversize material is crushed to produce additional material in the desired range. These granules contain 10% active ingredient.

EXAMPLE 4

Oil Suspension

| | |
|---|---|
| methyl 2-[[[[(4-methoxy-6-methyl-2-pyrimidinyl)amino]carbonyl]amino]sulfonyl]benzoate | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 5

Aqueous Suspension

| | |
|---|---|
| methyl 2-[[[[(4-methoxy-6-methyl-1,3,5-triazin-2-yl)amino]carbonyl]amino]sulfonyl]benzoate | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE 6

Wettable Powder

| | |
|---|---|
| methyl 2-[[[[(4,6-dimethoxy-2-pyrimidinyl)amino]carbonyl]amino]sulfonyl]benzoate | 95% |
| dioctyl sodium sulfosuccinate | 0.5% |
| sodium ligninsulfonate | 1.5% |
| synthetic fine silica | 3.0% |

The ingredients are blended and ground in a hammer-mill to produce particles, almost all of which are below 100 microns in size. This material is sifted through a U.S.S. No. 50 (0.3 mm) screen and then packaged.

EXAMPLE 7

Granule

| | |
|---|---|
| wettable powder of Example 6 | 8% |
| wettable powder of Example 2 | 2% |
| attapulgite granules (U.S.S. No. 20–40 mesh) | 90% |

A slurry of the wettable powders is sprayed onto the surface of the granules, which are being mixed in a blender. After the slurry has been added, the granules are removed from the blender, dried and packaged.

EXAMPLE 8

Oil Suspension

| | |
|---|---|
| 2,4-dichlorophenoxyacetic acid, butoxyethyl ester | 24.6% |
| methyl 2-[[[[(4-methoxy-6-methyl-1,3,5-triazin-2-yl)amino]carbonyl]amino]sulfonyl]benzoate | 0.4% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 9

Extruded Pellet

| | |
|---|---|
| methyl 2-[[[[(4,6-dimethoxy-2-pyrimidinyl)amino]carbonyl]amino]sulfonyl]benzoate | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammermilled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 10

Granule

| | |
|---|---|
| methyl 2-[[[[(4-methoxy-6-methyl-1,3,5-triazin-2-yl)carbonyl]amino]sulfonyl]benzoate | 10% |
| methyl 2-[[[[[(4,6-dimethoxy-2-pyrimidinyl)amino]carbonyl]amino-sulfonyl]methyl]benzoate | 50% |
| wetting agent | 1% |
| dispersing agent | 2% |
| crude ligninsulfonate salt (containing 5-20 of the natural sugars) | 10% |
| attapulgite clay | 27% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 11

Wettable Powder

| | |
|---|---|
| methyl 2-[[[[(4,6-dimethoxy-2-pyrimidinyl)-amino]carbonyl]amino]sulfonyl]benzoate | 80% |
| sodium alkylnaphthalenesulfonate | 2% |
| sodium ligninsulfonate | 2% |
| synthetic amorphous silica | 3% |
| kaolinite | 13% |

The ingredients are blended and then ground in a hammermill to produce particles with an average particle size less than 25 microns in diameter. The material is reblended and sifted through a U.S.S. No. 50 sieve (0.3 mm opening) before being packaged.

EXAMPLE 12

Wettable Powder

| | |
|---|---|
| methyl 2-[[[[(4-methoxy-6-methyl-1,3,5-triazin-2-yl)amino]carbonyl]amino]-sulfonyl]benzoate | 4% |
| methyl 2-[[[[[(4,6-dimethoxy-2-pyrimidinyl)-amino]carbonyl]amino]sulfonyl]methyl]benzoate | 36% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 13

Extruded Pellet

| | |
|---|---|
| methyl 2-[[[[(4-methoxy-6-methyl-1,3,5-triazin-2-yl)amino]carbonyl]-amino]sulfonyl]benzoate | 1% |
| methyl 2-[[[[[(4,6-dimethoxy-2-pyrimidinyl)amino]carbonyl]amino-sulfonyl]methyl]benzoate | 24% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammermilled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 14

Wettable Powder

| | |
|---|---|
| methyl 2-[[[[(4-methoxy-6-methyl-1,3,5-triazin-2-yl)amino]carbonyl]amino]sulfonyl]benzoate | 65% |
| dodecylphenol polyethylene glycol ether | 2% |
| sodium ligninsulfonate | 4% |
| sodium silicoaluminate | 6% |

-continued

| | |
|---|---|
| montmorillonite (calcined) | 23% |

The ingredients are thoroughly blended. The liquid surfactant is added by spraying upon the solid ingredients in the blender. After grinding in a hammermill to produce particles essentially all below 100 microns, the material is reblended and sifted through a U.S.S. No. 50 sieve (0.3 mm opening) and packaged.

EXAMPLE 15

Wettable Powder

| | |
|---|---|
| 2,4-dichlorophenoxyacetic acid, sodium salt | 49.5% |
| methyl 2-[[[[(4-methoxy-6-methyl-1,3,5-triazin-2-yl)amino]carbonyl]amino]sulfonyl]benzoate | 0.5% |
| sodium alkylnaphthalenesulfonate | 2% |
| low viscosity methyl cellulose | 2% |
| diatomaceous earth | 46% |

The ingredients are blended, coarsely hammermilled and then air milled to produce particles of active essentially all below 10 microns in diameter. The product is reblended before packaging.

EXAMPLE 16

Wettable Powder

| | |
|---|---|
| S-[(4-chlorophenyl)methyl]diethylcarbamothioate | 60% |
| methyl 2-[[[[(4-methoxy-6-methyl-1,3,5-triazin-2-yl)amino]carbonyl]amino]sulfonyl]benzoate | 1% |
| dodecylphenol polyethylene glycol ether | 2% |
| sodium ligninsulfonate | 4% |
| sodium silicoaluminate | 6% |
| sodium carbonate | 2% |
| montmorillonite (calcined) | 25% |

The ingredients are thoroughly blended. The liquid surfactant is added by spraying upon the solid ingredients in the blender. After grinding in a hammermill to produce particles essentially all below 100 microns, the material is reblended and sifted through a U.S.S. No. 50 sieve (0.3 mm opening) and packaged.

EXAMPLE 17

Wettable Powder

| | |
|---|---|
| S-1-methyl-1-phenylethylpiperidine-1-carbothioate | 60% |
| methyl 2-[[[[(4-methoxy-6-methyl-1,3,5-triazin-2-yl)amino]carbonyl]amino]sulfonyl]benzoate | 1% |
| dodecylphenol polyethylene glycol ether | 2% |
| sodium ligninsulfonate | 4% |
| sodium silicoaluminate | 6% |
| sodium carbonate | 2% |
| montmorillonite (calcined) | 25% |

The ingredients are thoroughly blended. The liquid surfactant is added by spraying upon the solid ingredients in the blender. After grinding in a hammermill to produce particles essentially all below 100 microns, the material is reblended and sifted through a U.S.S. No. 50 sieve (0.3 mm opening) and packaged.

EXAMPLE 18

Wettable Powder

| | |
|---|---|
| S-benzyl-N-ethyl-N-(1,2-dimethyl)-propylthiol carbamate | 60% |
| methyl 2-[[[[(4-methoxy-6-methyl-1,3,5-triazin-2-yl)amino]carbonyl]amino]sulfonyl]benzoate | 1% |
| dodecylphenol polyethylene glycol ether | 2% |
| sodium ligninsulfonate | 4% |
| sodium silicoaluminate | 6% |
| sodium carbonate | 2% |
| montmorillonite (calcined) | 25% |

The ingredients are thoroughly blended. The liquid surfactant is added by spraying upon the solid ingredients in the blender. After grinding in a hammermill to produce particles essentially all below 100 microns, the material is reblended and sifted through a U.S.S. No. 50 sieve (0.3 mm opening) and packaged.

EXAMPLE 19

Wettable Powder

| | |
|---|---|
| 1-($\alpha,\alpha$-dimethylbenzyl)-3-p-tolylurea | 60% |
| methyl 2-[[[[(4-methoxy-6-methyl-1,3,5-triazin-2-yl)amino]carbonyl]amino]sulfonyl]benzoate | 1% |
| dodecylphenol polyethylene glycol ether | 2% |
| sodium ligninsulfonate | 4% |
| sodium silicoaluminate | 6% |
| sodium carbonate | 2% |
| montmorillonite (calcined) | 25% |

The ingredients are thoroughly blended. The liquid surfactant is added by spraying upon the solid ingredients in the blender. After grinding in a hammermill to product particles essentially all below 100 microns, the material is reblended and sifted through a U.S.S. No. 50 sieve (0.3 mm opening) and packaged.

EXAMPLE 20

Wettable Powder

| | |
|---|---|
| Propanil | 60% |
| methyl 2-[[[[(4-methoxy-6-methyl-1,3,5-triazin-2-yl)amino]carbonyl]amino]sulfonyl]benzoate | 1% |
| dodecylphenol polyethylene glycol ether | 2% |
| sodium ligninsulfonate | 4% |
| sodium silicoaluminate | 6% |
| sodium carbonate | 2% |
| montmorillonite (calcined) | 25% |

The ingredients are thoroughly blended. The liquid surfactant is added by spraying upon the solid ingredients in the blender. After grinding in a hammermill to produce particles essentially all below 100 microns, the material is reblended and sifted through a U.S.S. No. 50 sieve (0.3 mm opening) and packaged.

Utility

The compounds of this invention are useful for the control of both upland and aquatic weeds in rice and upland cereal crops such as wheat and may be used in both transplanted and direct seeded rice. They are applied postemergence to the crop and may be applied from 7 days after transplanting or emergence to the time the rice crop has closed and no longer needs chemical weed control. They may be applied as a foliar spray in sufficient water to evenly distribute the treatment. Additives may be included in the spray to aid in penetration of the treatment.

According to the method of this invention in the case of rice, it is preferred to apply metsulfuron methyl in combination with propanil to the field when not in water-filled condition, after seeding or transplantation of rice. The optimal timing and method of application could be selected based on the location of the field, the timing of rice cultivation, the variety of rice, and the kind and growth condition of the weeds to be controlled.

Metsulfuron methyl in combination with propanil are particularly effective on sedges. In particular, metsulfuron methyl with propanil are useful for the control of troublesome broadleaf and grass weeds in direct-seeded upland rice (*Oryza sativa*) and in direct-seeded paddy rice. These mixtures could also be used for weed control in transplanted paddy rice and for weed control in cereal crops such as barley (*Hordeum vulgare*), triticale (*Triticum-Secale*), and wheat (*Triticum aestivum*) or in combination with commercial insecticides, fungicides or other herbicides. Examples of herbicides suitable for use with metsulfuron methyl and propanil are those herbicides of the triazine, triazole, imidazolinone, uracil, urea, amide, diphenylether, cineole, carbamate, dinitroaniline, and bipyridilium types.

The compounds of the invention are also effective in controlling broadleafed weeds and may be combined with other rice herbicides to broaden the spectrum of weed control. They are particularly effective on broadleafed weeds and sedges when combined with 2,4-dichlorophenoxyacetic acid (2,4-D), its agriculturally suitable esters or salts, or with benzsulfuron methyl.

Particularly useful combinations with 2,4-D comprise ratios of instant compound to 2,4-D of 4:125 to 1:625. Particularly useful combinations with benzsulfuron methyl comprise ratios of instant compound to benzsulfuron methyl of 1:2 to 1:50. The compounds of this invention may also be mixed with other rice herbicides including thiobencarb, esprocarb, dymron, dimepiperate, butachlor, molinate, ethyl 5-[[[[(4,6-dimethoxy-2-pyrimidinyl)amino]-carbonyl]amino]sulfonyl]-1-methyl-1-H-pyrazole-4-carboxylate, naproanilide, bentazon, cinmethylin, chlormethoxynl, quinchlorac, pretilachlor, MCPA, propanil, diflufenican, oxadiazon, and pyrazolate.

Except for the combination of metsulfuron methyl and propanil the application rates of the compounds of this invention may vary from 0.5 to 10 g/ha (preferably 1 to 5 g/ha) depending on weeds to be controlled, stage of growth of the crop and weeds, crop variety and environmental conditions at the time of application. One with ordinary skill in the art can select the rate to be used in each situation.

A herbicidally effective amount of the combination of metsulfuron methyl and propanil is generally the application of 500 to 25,000 g/ha. Preferably this amount is 625 to 6800 g/ha and most preferably this amount is 1500 to 5000 g/ha. What encompasses a herbicidally effective amount of the combination will vary according to the conditions of the field soil, weather conditions, location and others such as the crop and weeds and crop variety.

The amount of metsulfuron methyl relative to propanil is generally in a weight ratio of metsulfuron methyl to propanil of from 1:156 to 1:13600. Preferably this ratio is 1:200 to 1:4000, most preferably from 1:500 to 1:2000 and particularly 1:500 to 1:1000 of metsulfuron methyl to propanil by weight.

The examples below clearly demonstrate the utility of the compounds of this invention both alone and in mixtures.

EXAMPLES OF TEST A

Methyl 2-[[[[(4-methoxy-6-methyl-1,3,5-triazin-2-yl)amino]carbonyl]amino]sulfonyl]benzoate (Compound 1) and mixtures thereof with other compounds were applied as a spray (using a hand sprayer) to rice (either transplanted or direct seeded) in several rice growing areas in Southeast Asia and in the U.S. Tables 1–26 contain the results of these tests and clearly exemplify the utility of this invention. The details of each application are included in the appropriate table.

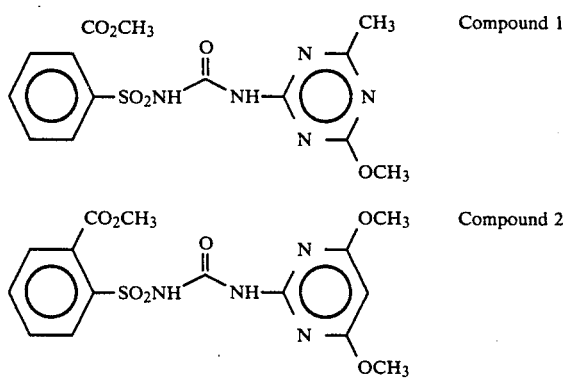

TABLE 1

| | Herbicidal efficacy[1] of Compound 1 in Thailand | | | | |
|---|---|---|---|---|---|
| TREAT-MENT[3] | RATE[2] (GAI/HA) | SZ[5] 2WAA[4] | CY[5] 2WAA[4] | SZ[5] 4WAA[4] | SZ[5] 6WAA[4] |
| Trial 1 | 2 | 100 | 33 | 100 | 100 |
| | 3 | 99 | 67 | 100 | 100 |
| | 4 | 100 | 67 | 100 | 100 |
| | 6 | 100 | 67 | 100 | 100 |
| Trial 2 | 2 | 97 | 0 | 99 | 99 |
| | 3 | 100 | 67 | 100 | 100 |
| | 4 | 99 | 33 | 99 | 100 |
| | 6 | 100 | 67 | 100 | 100 |

[1]100 denotes complete control, and 0 denotes no control.
[2]Application rate in grams active ingredient per hectare.
[3]Treatments applied at 36 days after seeding.
[4]WAA = weeks after application (evaluation).
[5]Abbreviations:
SZ = *Sphenoclea zeylanica*
CY = *Cyperus species*

TABLE 2

| | Effects of Compound 1 on rice growth in Thailand based on an average of three results | | | | |
|---|---|---|---|---|---|
| | | PHYTOTOXICITY[2] | | | |
| TREATMENT | GAI/HA[1] | 7 DAS[3] | 14 DAS[3] | 21 DAS[3] | 28 DAS[3] |
| Compound 1 | 3 | 1.67 | 1.0 | 0 | 0 |
| Compound 1 | 6 | 1.33 | 1.0 | 0 | 0 |
| 2,4-D (SODIUM | 600 | 2.33 | 1.33 | 0 | 0 |

TABLE 2-continued

Effects of Compound 1 on rice growth in Thailand based on an average of three results

| TREATMENT | GAI/HA[1] | PHYTOTOXICITY[2] | | | |
|---|---|---|---|---|---|
| | | 7 DAS[3] | 14 DAS[3] | 21 DAS[3] | 28 DAS[3] |
| SALT) | | | | | |
| 2,4-D (BUTYL ESTER) | 600 | 2.0 | 1.67 | 0 | 0 |
| Compound 1 + 2,4-D (SODIUM SALT) | 3 + 600 | 2.33 | 1.0 | 0.67 | 0 |
| Compound 1 + 2,4-D (BUTYL ESTER) | 3 + 600 | 2.67 | 1.33 | 0 | 0 |
| Compound 1 + PROPANIL | 3 + 600 | 2.0 | 1.0 | 0 | 0 |

[1]Application rate in grams active ingredient per hectare.
[2]Phytotoxicity scale is:
0 = no effect
3 = unacceptable
10 = 100% plant death
[3]DAS = days after seeding (application time).

TABLE 3

Herbicidal efficacy of Compound 1 and combinations with 2,4-D in Thailand based on an average of three results

| TREATMENT | RATE[1] (GAI/HA) | FIMBRISTYLIS MILIACEA CONTROL[2] | | | |
|---|---|---|---|---|---|
| | | 7 DAS[3] | 14 DAS[3] | 21 DAS[3] | 28 DAS[3] |
| Compound 1 | 3 | 53 | 20 | 0 | 0 |
| Compound 1 | 6 | 73 | 40 | 0 | 0 |
| 2,4-D (SODIUM SALT) | 600 | 96 | 95 | 93 | 98 |
| 2,4-D (BUTYL ESTER) | 600 | 94 | 98 | 60 | 43 |
| Compound 1 + 2,4-D (SODIUM SALT) | 3 + 600 | 97 | 90 | 92 | 100 |
| Compound 1 2,4-D (BUTYL ESTER | 3 + 600 | 70 | 47 | 27 | 43 |

[1]Application rate in grams active ingredient per hectare.
[2]% Control evaluated at 6 weeks after application.
[3]DAS = days after seeding (application time).

TABLE 4

Effects of Compound 1 on rice growth in Thailand based on an average of three results

| TREATMENTS | GAI/HA[1] | PHYTOTOXICITY[2] | | | |
|---|---|---|---|---|---|
| | | 7 DAS[3] | 14 DAS[3] | 21 DAS[3] | 28 DAS[3] |
| Compound 1 | 3 | 1.67 | 1.0 | 0.67 | 0 |
| Compound 1 | 6 | 1.67 | 1.0 | 1.0 | 0 |
| 2,4-D (SODIUM SALT) | 600 | 5.0 | 3.67 | 3.0 | 1 |
| 2,4-D (BUTYL ESTER) | 600 | 3.67 | 2.33 | 2.67 | 3 |
| Compound 1 + 2,4-D (SODIUM SALT) | 3 + 600 | 4.67 | 2.67 | 4.33 | 1.67 |
| Compound 1 + 2,4-D (BUTYL ESTER) | 3 + 600 | 3.33 | 2.33 | 4.0 | 2.0 |

[1]Application rate in grams active ingredient per hectare.
[2]Phytotoxicity scale is:
0 = no effect
3 = unacceptable
10 = 100% plant death
[3]DAS = days after seeding (application time).

TABLE 5

Herbicidal efficacy of Compound 1 in relation to application timing in Indonesia

| TREATMENT[1] | RATES[2] GAI/HA[2] | MV[3] 1[4] | 2 | 3 | CI[3] 1 | 2 | 3 | PS[3] 1 | 2 | 3 | RICE 1 | 2 | 3 |
|---|---|---|---|---|---|---|---|---|---|---|---|---|---|
| | | | | | | % CONTROL | | | | | | | |
| Compound 1 (3 WAT)[5] | 2 | 80 | 80 | 100 | 0 | 0 | 0 | 0 | 0 | 0 | 0 | 0 | 0 |
| | 3 | 80 | 100 | 100 | 20 | 0 | 0 | 0 | 0 | 0 | 0 | 0 | 0 |
| | 4 | 100 | 100 | 100 | 20 | 0 | 0 | 0 | 0 | 0 | 0 | 0 | 0 |
| | 6 | 80 | 100 | 100 | 20 | 0 | 0 | 0 | 0 | 0 | 0 | 0 | 0 |
| | 8 | 100 | 100 | 100 | 20 | 0 | 0 | 0 | 0 | 0 | 0 | 0 | 0 |
| Compound 1 (4 WAT) | 2 | 80 | 100 | 100 | 0 | 0 | 0 | 0 | 0 | 0 | 0 | 0 | 0 |
| | 3 | 80 | 100 | 100 | 0 | 0 | 0 | 0 | 0 | 0 | 0 | 10 | 0 |
| | 4 | 80 | 100 | 100 | 20 | 20 | 0 | 0 | 0 | 0 | 20 | 20 | 0 |
| | 6 | 80 | 100 | 100 | 20 | 20 | 0 | 0 | 0 | 0 | 20 | 20 | 0 |
| | 8 | 100 | 100 | 100 | 20 | 20 | 0 | 0 | 0 | 0 | 20 | 20 | 0 |
| Compound 1 (5 WAT) | 2 | 80 | 80 | 80 | 0 | 0 | 0 | 0 | 0 | 0 | 10 | 0 | 0 |
| | 3 | 80 | 100 | 100 | 50 | 20 | 0 | 0 | 0 | 0 | 10 | 0 | 0 |
| | 4 | 80 | 100 | 100 | 60 | 30 | 0 | 0 | 0 | 0 | 30 | 0 | 0 |
| | 6 | 80 | 100 | 100 | 60 | 40 | 0 | 0 | 0 | 0 | 0 | 0 | 0 |
| | 8 | 100 | 100 | 100 | 60 | 60 | 30 | 0 | 0 | 0 | 30 | 10 | 0 |

[1]Plots drained prior to application and reflooded 3 days later.
[2]Application rate in grams active ingredient per hectare.
[3]Abbreviations:
MV = *Monochoria vaginalis*
CI = *Cyperus iria*
PS = *Pistia stratioides*
[4]Weeks after application (evaluation).
[5]WAT = weeks after transplanting (application).

TABLE 6

Herbicidal efficacy of Compound 1 in Indonesia

| TREATMENT[1] | RATES[2] GAI/HA[2] | SM[3] 2[4] | 5 | 7 | SJ 2 | 5 | 7 | MV 2 | 5 | 7 | EC 2 | 5 | 7 | RICE 2 |
|---|---|---|---|---|---|---|---|---|---|---|---|---|---|---|
| | | | | | | | % CONTROL | | | | | | | |
| Compound 1 | 3 | 30 | 70 | 80 | 60 | 90 | 70 | 100 | 100 | 100 | 20 | 30 | 0 | 10 |
| | 4 | 40 | 70 | 80 | 60 | 100 | 70 | 90 | 100 | 100 | 20 | 30 | 0 | 10 |
| | 6 | 30 | 90 | 90 | 90 | 100 | 80 | 100 | 100 | 100 | 20 | 30 | 0 | 10 |
| | 8 | 40 | 80 | 90 | 80 | 100 | 80 | 100 | 100 | 100 | 20 | 30 | 0 | 10 |
| Compound 1 + HERBAZOL[5] | 3 + 515 | 20 | 70 | 80 | 90 | 100 | 100 | 100 | 100 | 100 | 20 | 30 | 0 | 10 |
| | 4 + 515 | 30 | 90 | 80 | 80 | 90 | 100 | 90 | 100 | 100 | 20 | 30 | 0 | 10 |
| | 6 + 515 | 30 | 70 | 90 | 80 | 100 | 80 | 100 | 100 | 100 | 20 | 40 | 0 | 10 |
| HERBAZOL | 515 | 10 | 50 | 30 | 80 | 100 | 90 | 80 | 50 | 50 | 20 | 30 | 0 | 10 |
| | 1033 | 0 | 50 | 30 | 100 | 100 | 90 | 100 | 50 | 50 | 20 | 30 | 0 | 10 |

[1]Application was at 2 weeks after transplanting. Plots were drained prior to application and reflooded 3 days after application.
[2]Application rate in grams active ingredient per hectare.
[3]Abbreviations:
SM = *Salvinia molesta*
MV = *Monochoria vaginalis*
SJ = *Scripus juncoides*
EC = *Echinochloa crus-galli*
[4]Weeks after application (evaluation).
[5]2,4-D amine salt.

TABLE 7

Effects of herbicide treatments on the crop tolerance of transplanted rice

| TREATMENTS GAI/HA[2] | CROP TOLERANCE[1] 1 WAA[3] | 2WAA | 4WAA | 6WAA |
|---|---|---|---|---|
| Compound 1 | | | | |
| 3 | 0 | 0 | 0 | 0 |
| 4 | 0 | 0 | 0 | 0 |
| 6 | 1 | 0 | 0 | 0 |
| 8 | 1 | 1 | 0 | 0 |
| Compound 1 + HERBAZOL[4] | | | | |
| 3 + 515 | 0 | 0 | 0 | 0 |
| 4 + 515 | 1 | 0 | 0 | 0 |
| 6 + 515 | 2 | 1 | 0 | 0 |
| HERBAZOL | | | | |
| 515 | 1 | 1 | 0 | 0 |
| 1,030 | 2 | 2 | 0 | 0 |

[1]Crop tolerance rating: 0 = no effect; 10 = completely killed
[2]Application rate in grams active ingredient per hectare.
[3]WAA = weeks after application (evaluation).
[4]2,4-D amine salt.

TABLE 8

Herbicidal efficacy of Compound 1 and combinations with 2,4-D in Malaysia

| TREATMENT[1] | RATES[2] GAI/HA | SG[3] | MV | SZ | CD | FM | MC |
|---|---|---|---|---|---|---|---|
| | | | | % CONTROL | | | |
| Com- | 1 | 80 | 95 | 0 | 0 | 0 | 20 |

-continued

Herbicidal efficacy of Compound 1 and combinations with 2,4-D in Malaysia

| TREATMENT[1] | RATES[2] GAI/HA | SG[3] | MV | SZ | CD | FM | MC |
|---|---|---|---|---|---|---|---|
| pound 1 | 2 | 100 | 95 | 100 | 100 | 100 | 95 |
|  | 3 | 95 | 100 | 100 | 95 | 50 | 100 |
|  | 4 | 95 | 100 | 100 | 100 | 50 | 95 |
|  | 5 | 100 | 100 | 100 | 100 | 20 | 100 |
| 2,4-D[4] | 500 | 50 | 90 | 100 | 95 | 100 | 0 |
|  | 1000 | 75 | 100 | 100 | 100 | 100 | 0 |
| Compound 1 + 2,4-D | 1 + 500 | 90 | 95 | 100 | 67 | 100 | 95 |
|  | 2 + 500 | 95 | 100 | 100 | 95 | 100 | 100 |
|  | 3 + 500 | 100 | 100 | 100 | 100 | 100 | 100 |
|  | 4 + 500 | 100 | 100 | 100 | 100 | 100 | 100 |
|  | 5 + 500 | 100 | 100 | 100 | 95 | 95 | 100 |

[1]Applications at 30 days after seeding. Evaluation at 22 days after treatment.
[2]Application rate in grams active ingredient per hectare.
[3]Abbreviations:
SG = Scripus grossus
MV = Monochoria vaginalis
SZ = Sphenoclea zeylanica
CD = Cyperus difformis
FM = Fimbristylis miliacea
MC = Marsilea crenata
[4]2,4-D was dimethylamine salt.

TABLE 9

Broadleaf weed control with a late-post application of Compound 1 in Beaumont, Texas

| RATE G/HA | RICE | EC | SE | AI | CC | COM | EA | SEDGE |
|---|---|---|---|---|---|---|---|---|
|  | % INJURY OR CONTROL | | | | | | | |
| 3 | 3 | 26 | 68 | 68 | 11 | 13 | 13 | 43 |
| 6 | 5 | 30 | 62 | 62 | 19 | 24 | 23 | 56 |
| 12 | 6 | 24 | 46 | 46 | 18 | 23 | 15 | 56 |

1. Compound 1 applied with 0.25% AG-98 wetting agent.
2. Application rate is stated in units of grams active ingredient per hectare.
3. Treated 30 days after seeding (24 days after emergence) to wet soil; flooded 24 days after emergence (6 days after application); evaluated at 70 days after seeding.
4. Abbreviations:
EC = Echinochloa colonum
SE = Sesbania exaltata
AI = Aeschynomene indica
CC = Caperonia castaniifolia
COM = Commelina communis
EA = Eclipta alba
SEDGE = Annual sedge (?)

TABLE 10

Field Test Results of Compound 1 + Bensulfuron methyl for weed control in direct seeded rice

| TREATMENTS | GAI/HA[1] | WEEDS CONTROL[2] at 4 WAA | | | YIELD TONS/ HA |
|---|---|---|---|---|---|
|  |  | SZ[3] | CI[4] | MC[5] |  |
| COMPOUND 1 | 2 | 7.93 | 0 | 10 | 3.62 |
| COMPOUND 1 | 4 | 9.33 | 0 | 10 | 3.62 |
| BENSULFURON METHYL | 10 | 0 | 2 | 0 | 3.04 |
| BENSULFURON METHYL | 20 | 6 | 8 | 3.33 | 3.34 |
| COMPOUND 1 + BENSULFURON METHYL | 2 + 10 | 9.1 | 6.33 | 10 | 3.64 |
| COMPOUND 1 + BENSULFURON METHYL | 4 + 10 | 9.93 | 5.0 | 10 | 3.79 |
| COMPOUND 1 + BENSULFURON METHYL | 2 + 20 | 8.33 | 5.67 | 10 | 3.50 |
| COMPOUND 1 + BENSULFURON METHYL | 4 + 20 | 10 | 9.0 | 10 | 3.72 |
| UNTREATED | — | 0 | 0 | 0 | 2.75 |

[1]Application rate is stated in units of grams active ingredient per hectare.
[2]10 is complete control, and 0 is no control, WAA = weeks after application (evaluation).
[3]SZ = Sphenoclea zeylanica
[4]CI = Cyperus iria
[5]MC = Marsilea crenata

TABLE 11

Field Test Results of Compound 1 + Bensulfuron methyl applied at 7 DAS[1] for weed control in direct seeded rice

| TREATMENTS | GM.A.I.[2]/ HA | PHYTO[3] at 2 WAA | WEED CONTROL[4] at 6 WAA | | YIELD TONS/ HA |
|---|---|---|---|---|---|
|  |  |  | SZ[5] | CD[6] |  |
| COMPOUND 1 | 4 | 0 | 10 | 10 | 4.90 |
| BENSULFURON METHYL | 10 | 0 | 10 | 10 | 4.92 |
|  | 15 | 0 | 10 | 10 | 4.99 |
|  | 20 | 0 | 10 | 10 | 5.01 |
|  | 30 | 0 | 10 | 10 | 4.67 |
| COMPOUND 1 + BENSULFURON METHYL | 4 + 10 | 0 | 10 | 10 | 5.35 |
|  | 4 + 15 | 0 | 10 | 10 | 4.56 |
|  | 4 + 20 | 0 | 10 | 10 | 4.73 |
| COMPOUND 1 + 2,4-D (NA)[7] | 4 + 750 | 0 | 10 | 10 | 4.81 |
| 2,4-D (NA) | 1,500 | 0 | 6.0 | 10 | 4.13 |
| UNTREATED | — | 0 | 0 | 0 | 3.55 |

[1]DAS = Days after seeding
[2]Application rate is stated in units of grams active ingredient per hectare.
[3]Phytotoxicity is rated on a scale of:
0 = no effect
3 = unacceptable
10 = 100% plant death
[4]Control is rated on a scale of:
0 = no control
10 = complete control
WAA = weeks after application
[5]SZ = Sphenoclea zeylanica
[6]CD = Cyperus difformis
[7]Sodium salt of 2,4-D.

TABLE 12

Field Test Results of Compound 1 + Bensulfuron methyl applied at 18 DAS[1] for weed control in direct seeded rice

| TREATMENTS | GM.A.I.[2]/ HA | PHYTO[3] at 2 WAA | WEED CONTROL[4] at 6 WAA | | | | YIELD TONS/ HA |
|---|---|---|---|---|---|---|---|
| | | | SZ[5] | CI[6] | FM[7] | JL[8] | |
| COMPOUND 1 | 4 | 0 | 6.33 | 0.33 | 0 | 7.67 | 4.65 |
| BENSULFURON | 10 | 0 | 5.67 | 6.67 | 10 | 8.0 | 4.61 |
| METHYL | 15 | 0 | 6.67 | 9.0 | 9.67 | 7.67 | 4.49 |
| | 20 | 0 | 5.67 | 9.33 | 10 | 9.50 | 4.61 |
| | 30 | 0 | 9.67 | 9.67 | 10 | 8.67 | 5.17 |
| COMPOUND 1 + | 4 + 10 | 0 | 10 | 8.83 | 10 | 9.50 | 5.40 |
| BENSULFURON | 4 + 15 | 0 | 10 | 10 | 10 | 10 | 5.40 |
| METHYL | 4 + 20 | 0 | 10 | 9.63 | 9.67 | 10 | 5.06 |
| COMPOUND 1 + 2,4-D (NA)[9] | 4 + 750 | 0 | 9.0 | 9.67 | 9.0 | 10 | 5.04 |
| 2,4-D (NA) | 1,500 | 0 | 4.67 | 9.33 | 9.33 | 10 | 4.59 |
| UNTREATED | — | 0 | 0 | 0 | 0 | 0 | 4.31 |

[1]DAS = Days after seeding
[2]Application rate is stated in units of grams active ingredient per hectare.
[3]Phytotoxicity is rated on a scale of:
0 = no effect
3 = unacceptable
10 = 100% plant death
WAA = weeks after application
[4]Control is rated on a scale of:
0 = no control
10 = complete control
WAA = weeks after application
[5]SZ = *Sphenoclea zeylanica*
[6]CI = *Cyperus iria*
[7]FM = *Fimbristylis miliacea*
[8]JL = *Jussiaea linifolia*
[9]Sodium salt of 2,4-D.

TABLE 13

Field Test Results of Compound 1 + Bensulfuron methyl applied at 25 DAS[1] for weed control in direct seeded rice

| TREATMENTS | GM.A.I.[2]/ HA | PHYTO[3] at 2 WAA | WEED CONTROL[4] at 6 WAA | | YIELD TONS/ HA |
|---|---|---|---|---|---|
| | | | SZ[5] | CI[6] | |
| COMPOUND 1 | 4 | 0 | 9.53 | 0 | 5.04 |
| BENSULFURON | 10 | 0 | 9.17 | 9.67 | 4.77 |
| METHYL | 15 | 0 | 9.80 | 9.83 | 4.85 |
| | 20 | 0 | 9.50 | 10 | 5.40 |
| | 30 | 0 | 9.93 | 10 | 5.51 |
| COMPOUND 1 + | 4 + 10 | 0 | 10 | 9.5 | 5.57 |
| BENSULFURON | 4 + 15 | 0 | 10 | 10 | 5.51 |
| METHYL | 4 + 20 | 0 | 9.83 | 10 | 5.34 |
| COMPOUND 1 + 2,4-D (NA)[7] | 4 + 750 | 0 | 10 | 10 | 4.83 |
| 2,4-D (NA) | 1,500 | 0 | 6.67 | 10 | 4.59 |
| UNTREATED | — | 0 | 0 | 0 | 4.27 |

[1]DAS = Days after seeding
[2]Application rate is stated in units of grams active ingredient per hectare.
[3]Phytotoxicity is rated on a scale of:
0 = no effect
3 = unacceptable
10 = 100% plant death
WAA = weeks after application
[4]Control is rated on a scale of:
0 = no control
10 = complete control
WAA = weeks after application
[5]SZ = *Sphenoclea zeylanica*
[6]CI = *Cyperus iria*
[7]Sodium salt of 2,4-D.

TABLE 14

Field Test Results of Compound 1 + Bensulfuron Methyl, Applied 7 DAS[1], for weed control in direct seeded rice in the Philippines, average of 3 repetitions

| TREATMENTS G AI/HA[2] | PHYTO[3] (1–9) 30 DAA | % WEED COVER 47 DAA | % BYG[4] COVER 47 DAA | % SEDGE COVER 47 DAA |
|---|---|---|---|---|
| COMPOUND 1 1.65 + BENSULFURON METHYL 8.25 | 1.7 | 20 | 18 | 5 |
| COMPOUND 1 2.40 + BENSULFURON METHYL 12.0 | 2.3 | 28 | 17 | 3 |
| COMPOUND 1 3.33 + BENSULFURON METHYL 16.5 | 4.3 | 3 | 3 | 0.5 |
| COMPOUND 1 1.65 | 2 | 29 | 26 | 5 |
| COMPOUND 1 2.40 | 2.3 | 35 | 35 | 6 |
| COMPOUND 1 3.33 | 3.3 | 35 | 35 | 4 |
| COMPOUND 1 8.25 | 1.3 | 29 | 29 | 4 |
| COMPOUND 1 12.0 | 1 | 20 | 17 | 2 |
| COMPOUND 1 16.50 | 1.7 | 28 | 28 | 2 |
| Untreated Check | 1 | 46 | 27 | 18 |

[1]DAS = Days after seeding
[2]Application rate is stated in units of grams active ingredient per hectare.
[3]Phytotoxicity is rated on a scale of:
1 = no effect
9 = 100% plant death
DAA = days after application
[4]Barnyardgrass (*Echinochloa crus-galli*)

TABLE 15

Effects of Compound 1 in Combination With Thiobencarb, Dimepiperate, Esprocarb and Dymron on Rice Growth

| TREATMENT | RATE GAI/HA[1] | CROP TOLERANCE[5] (Nihonbare) VA[2] | PH[3] | DW[4] |
|---|---|---|---|---|
| Compound 1 | 4 | 0 | 103 | 107 |
| Compound 1 and Thiobencarb | 4 + 2100 | 0 | 102 | 110 |
| Compound 1 and Dimepiperate | 4 + 3000 | 0 | 104 | 110 |
| Compound 1 and Esprocarb | 4 + 2100 | 0 | 101 | 106 |
| Compound 1 and Dymron | 4 + 2100 | 0 | 102 | 101 |
| Compound 1 | 8 | 3 | 95 | 83 |
| Compound 1 and Thiobencarb | 8 + 2100 | 0 | 101 | 108 |
| Compound 1 and Dimepiperate | 8 + 3000 | 0 | 103 | 103 |
| Compound 1 and Esprocarb | 8 + 2100 | 0.5 | 99 | 98 |
| Compound 1 and Dymron | 8 + 2100 | 1.0 | 100 | 96 |
| Thiobencarb | 2100 | 0 | 102 | 112 |
| Dimepiperate | 3000 | 0 | 102 | 106 |
| Esprocarb | 2100 | 0 | 92 | 94 |
| Dymron | 2100 | 0 | 102 | 107 |
| Untreated | — | 0 | 100 | 100 |

[1]Application rate in grams active ingredient per hectare.
[2]Visual crop injury (relative to untreated check) scale of:
0 to 100%
0 = no injury
100 = 100% plant death.
[3]Plant Height (relative to untreated check) on scale of: 0 to 100%.
[4]Dry Weight (relative to untreated check) on scale of: 0 to 100%.
[5]Crop tolerance - Compounds were applied to transplanted rice 5 days after transplanting (var. Nihonbare) 2.0 to 2.2 leaf stage. Ratings were taken 15 days after application. Results are the average of three replications.

TABLE 16

Herbicidal Efficacy of Compound 1 in United States

| RATE GAI/HA[3] | % CONTROL OR INJURY[1] EA[2] | SE[2] | RICE |
|---|---|---|---|
| 7 | 97 | 97 | 3 |
| 14 | 98 | 98 | 10 |
| 21 | 98 | 98 | 5 |

[1]Evaluations made 57 days after application.
[2]Abbreviations: EA = *Eclipta alba*
SE = *Sesbania exaltata*
[3]Application rate in grams active ingredient per hectare.

TABLE 17

Herbicidal Efficacy of Compound 1 and 2,4-D in Thailand

| TREATMENT | RATE GAI/HA[3] | % CONTROL OR INJURY[1] CD | LL | MC[2] | SZ | RICE |
|---|---|---|---|---|---|---|
| Compound 1 | 4 | 100 | 87 | 100 | 100 | 16.6 |
| Compound 1 + 2,4-D | 4 750 | 100 | 100 | 100 | 100 | 24.4 |

[1]Evaluations made 14 days after treatment.
[2]Abbreviations:
CD = *Cyperus difformis*
LL = *Ludwigia linifolia*
MV = *Monochoria vaginalia*
SZ = *Sphenoclea zeylanica*
[3]Application rate in grams active ingredient per hectare.

TABLE 18

Herbicidal Efficacy of Compound 1, Benzsulfuron methyl and 2,4-D in Thailand

| TREATMENT | RATE GAI/HA[3] | % CONTROL OR INJURY[1] CD | LL | SZ | RICE |
|---|---|---|---|---|---|
| Compound 1 | 4 | 100 | 100 | 98 | 0 |
| Bensulfuron methyl | 10 | 100 | 100 | 99 | 0 |
|  | 15 | 100 | 100 | 100 | 0 |
|  | 20 | 100 | 100 | 100 | 0 |
| Compound 1 + Bensulfuron methyl | 4 10 | 100 | 100 | 100 | 0 |
| Compound 1 + Bensulfuron methyl | 4 15 | 100 | 100 | 100 | 0 |
| Compound 1 + Bensulfuron methyl | 4 20 | 100 | 100 | 100 | 0 |
| 2,4-D | 1500 | 100 | 100 | 90 | 0 |
| Compound 1 + 2,4-D | 4 750 | 100 | 100 | 100 | 0 |

[1]Evaluation made 13 days after treatment.
[2]Abbreviations: CD = *Cyperus difformis*
LL = *Ludwigia linifolia*
SZ = *Sphenoclea Zeylanica*
[3]Application rate in grams active ingredient per hectare.

TABLE 19

Herbicidal Efficacy of Compound 1
Benzsulfuron Methyl and 2,4-D in Thailand

| TREATMENT | RATE GAI/HA[3] | % CONTROL OR INJURY[1] | | | |
|---|---|---|---|---|---|
| | | CD | LL | SZ | RICE |
| Compound 1 | 4 | 100 | 93 | 93 | 0 |
| Bensulfuron | 10 | 100 | 100 | 88 | 0 |
| methyl | 15 | 100 | 100 | 100 | 0 |
| | 20 | 100 | 100 | 100 | 0 |
| Compound 1 + | 4 | 100 | 100 | 100 | 0 |
| Bensulfuron methyl | 10 | | | | |
| Compound 1 + | 4 | 100 | 100 | 100 | 0 |
| Bensulfuron methyl | 15 | | | | |
| Compound 1 + | 4 | 100 | 100 | 100 | 0 |
| Bensulfuron methyl | 20 | | | | |
| 2,4-D | 1500 | 100 | 97 | 86 | 0 |
| Compound 1 + 2,4-D | 4 750 | 100 | 100 | 100 | 0 |

[1]Evaluation made 13 days after treatment.
[2]Abbreviations: CD = *Cuperus difformis*
LL = *Ludwigia linifolia*
SZ = *Sphenoclea zeylanica*
[3]Application rate in grams active ingredient per hectare.

TABLE 20

Herbicidal Efficacy of Compound 1,
benzsulfuron methyl and 2,4-D in Thailand

| TREATMENT | RATE GAI/HA[3] | % CONTROL OR INJURY[1] | | | | |
|---|---|---|---|---|---|---|
| | | CI | FM | LL | SZ | RICE |
| Compound 1 | 4 | 0 | 0 | 67 | 60 | 0 |
| Bensulfuron | 10 | 77 | 80 | 80 | 23 | 0 |
| methyl | 15 | 90 | 100 | 80 | 60 | 0 |
| | 20 | 95 | 100 | 87 | 53 | 0 |
| Compound 1 + | 4 | 95 | 100 | 98 | 97 | 0 |
| Bensulfuron methyl | 10 | | | | | |
| Compound 1 + | 4 | 100 | 100 | 100 | 100 | 0 |
| Bensulfuron methyl | 15 | | | | | |
| Compound 1 + | 4 | 98 | 90 | 100 | 97 | 0 |
| Bensulfuron methyl | 20 | | | | | |
| Compound 1 2,4-D | 4 750 | 95 | 90 | 100 | 88 | 0 |
| 2,4-D | 1500 | 100 | 100 | 100 | 33.3 | 0 |

[1]Evaluations made 14 days after treatment.
[2]Abbreviations: CI = *Cuperus iria*
FM = *Fimbristylis miliacea*
LL = *Ludwigia linifolia*
SZ = *Sphenoclea zeylanica*
[3]Application rate in grams active ingredient per hectare.

TABLE 21

Herbicidal Efficacy of Compound 1
and 2,4-D in Malaysia

| TREATMENT | RATE GAI/HA[3] | % CONTROL OR INJURY[1] | | | | | |
|---|---|---|---|---|---|---|---|
| | | FM[2] | LA | MC | MV | SG | SS |
| Compound 1 + 2,4-D | 4 + 330 | 28 | 89 | 78 | 100 | 100 | 63 |
| Compound 1 + 2,4-D | 4 + 500 | 28 | 88 | 98 | 100 | 100 | 62 |
| 2,4-D | 1000 | 73 | 93 | 56 | 100 | 74 | 55 |

[1]Evaluations made 42 days after treatment.
[2]Abbreviations: FM = *Fimbristylis miliacea*
LA = *Ludwigia adscendens*
MC = *Masilea crenata*
MV = *Monochoria vaginalis*
SG = *Saggittaria guayanensis*
SS = *Scirpus* spp.
[3]Application rate in grams active ingredient per hectare.

TABLE 22

Effects of Compound 1 in Combination
With Thiobencarb and Bensulfuron Methyl
on Rice Growth

| TREATMENT | RATE GAI/HA[1] | CROP TOLERANCE[5] | | |
|---|---|---|---|---|
| | | VA[2] | PH[3] | DW[4] |
| Compound 1 | 8 | 0.5 | 99 | 92 |
| Compound 1 and Thiobencarb | 8 + 2100 | 1.5 | 93 | 87 |
| Compound 1 and Bensulfuron methyl | 8 + 75 | 3.5 | 62 | 65 |
| Compound 1 and Thiobencarb, and Bensulfuron methyl | 8 + 2100 + 75 | 1.5 | 94 | 88 |
| Bensulfuron | 75 | 3.5 | 84 | 76 |
| Bensulfuron methyl and Thiobencarb | 75 + 2100 | 1.5 | 94 | 83 |
| Thiobencarb | 2100 | 0 | 99 | 99 |
| Untreated | — | 0 | 100 | 100 |

[1]Application rate in grams active ingredient per hectare.
[2]Visual crop injury (relative to untreated check) on scale of:
0 to 100%
0 = no injury
100 = 100% plant death.
[3]Plant height (relative to untreated check) on scale of: 0 to 100%.
[4]Dry weight (relative to untreated check) on scale of: 0 to 100%.
[5]Crop tolerance - compounds were applied to transplanted rice 7 days after transplanting (var. Koshihikari) at the 2.0 to 2.2 leafstage. Ratings were made 21 days after application. Results are the average of three replications.

TABLE 23

Effects of Compound 1 in Combination
With Bensulfuron Methyl and Thiobencarb
or Pretilachlor on Rice Growth

| TREATMENT | RATE GAI/HA[1] | CROP TOLERANCE[5] | | |
|---|---|---|---|---|
| | | VA[2] | PH[3] | DW[4] |
| Compound 1 | 2 | 3 | 86 | 73 |
| Bensulfuron Methyl | 25 | 2.5 | 89 | 79 |
| Compound 1 and Bensulfuron methyl | 2 + 25 | 3.5 | 86 | 69 |
| Compound 1 Bensulfuron methyl and Thiobencarb | 8 + 25 + 2100 | 2.5 | 87 | 73 |
| Compound 1 and Bensulfuron methyl and Pretilachlor | 2 + 25 + 600 | 2.5 | 90 | 72 |
| Thiobencarb | 2100 | 2 | 93 | 81 |
| Pretilachlor | 600 | 3 | 87 | 71 |
| Untreated | — | 0 | 100 | 100 |

[1]Application rate in grams active ingredient per hectare.
[2]Visual crop injury (relative to untreated check) on scale of:
0 to 100%
0 = no injury
100 = 100% plant death.
[3]Plant height (relative to untreated check) on scale of: 0 to 100%.
[4]Dry weight (relative to untreated check) on scale of: 0 to 100%.
[5]Crop tolerance - compounds were applied to transplanted rice 7 days after transplanting (var. Koshihikari) at the 2.0 to 2.2 leaf stage. Ratings were made 21 days after application. Results are the average of three replications.

TABLE 24

Effects of Compound 1 in Combination With Bensulfuron Methyl and Thiobencarb or Pretilachlor on Weed Control

| TREATMENTS | RATE GAI/HA[1] | WEED CONTROL RATINGS[2] | | | | | | |
|---|---|---|---|---|---|---|---|---|
| | | EO[3] | CD[4] | MV[5] | BL[6] | SJ[7] | SP[8] | CS[9] |
| COMPOUND 1 | 2 | 1 | 10 | 10 | 10 | 7 | 8 | 1 |
| BENSULFURON METHYL | 25 | 1 | 1 | 10 | 10 | 5 | 8.5 | 6 |
| COMPOUND 1 AND BENSULFURON METHYL | 2 + 25 | 4 | 10 | 10 | 10 | 9 | 8.5 | 8 |
| COMPOUND 1, BENSULFURON METHYL AND THIOBENCARB | 2 + 25 + 2100 | 8 | 10 | 10 | 10 | 9 | 8.5 | 9 |
| COMPOUND 1, BENSULFURON METHYL AND PRETILACHLOR | 2 + 25 + 600 | 10 | 10 | 10 | 10 | 9 | 9 | 8 |
| THIOBENCARB | 2100 | 10 | 10 | 10 | 9 | 7 | 0 | 9 |
| PRETILACHLOR | 600 | 10 | 10 | 5 | 10 | 5 | 3 | 3 |
| UNTREATED | — | 0 | 0 | 0 | 0 | 0 | 0 | 0 |

[1]Application rate in grams active ingredient per hectare.
[2]Visual weed control (relative to untreated check) on scale of:
0 to 10
0 = no injury
10 = complete control.
[3]EO = Echinochloa oryzicola
[4]CD = Cyperus difformis
[5]MV = Monochoria vaginalis
[6]BL = Lindernia pyxidaria
[7]SJ = Scirpus juncoides
[8]SP = Sagittaria pygmaea
[9]CS = Cyperus serotinus
[10]Weeds were treated at the 1.0 leaf stage and evaluated four weeks later. Results are the average of two replications.

TABLE 25

Effects of Compound 1 in Combination With Bensulfuron Methyl and Thiobencarb or Pretilachlor on Weed Control

| TREATMENTS | RATE GM.A.I.[1] | WEED CONTROL RATINGS[2] | | | | | | |
|---|---|---|---|---|---|---|---|---|
| | | EO[3] | CD[4] | MV[5] | BL[6] | SJ[7] | SP[8] | CS[9] |
| COMPOUND 1 | 2 | 1 | 7 | 10 | 10 | 6 | 8 | 0 |
| BENSULFURON METHYL | 25 | 1 | 10 | 9 | 9 | 5 | 8 | 2 |
| COMPOUND 1 AND BENSULFURON METHYL | 2 + 25 | 3 | 10 | 10 | 10 | 8.5 | 8.5 | 3 |
| COMPOUND 1, BENSULFURON METHYL AND THIOBENCARB | 2 + 25 + 2100 | 5 | 10 | 10 | 10 | 9 | 8 | 6 |
| COMPOUND 1, BENSULFURON METHYL AND PRETILACHLOR | 2 + 25 + 600 | 6 | 10 | 10 | 10 | 9 | 8 | 3 |
| THIOBENCARB | 2100 | 6 | 10 | 10 | 9.5 | 8.5 | 0 | 2 |
| PRETILACHLOR | 600 | 7 | 10 | 3 | 7 | 2 | 6 | 3 |
| UNTREATED | — | 0 | 0 | 0 | 0 | 0 | 0 | 0 |

[1]Application rate in grams active ingredient per hectare.
[2]Visual weed control (relative to untreated check) on scale of:
0 to 10
0 = no injury
10 = complete control.
[3]EO = Echinochloa oryzicola
[4]CD = Cyperus difformis
[5]MV = Monochoria vaginalis
[6]BL = Lindernia pyxidaria
[7]SJ = Scirpus juncoides
[8]SP = Sagittaria pygmaea
[9]CS = Cyperus serotinus
[10]Weeds were treated at the 2.0 leaf stage and evaluated four weeks later. Results are the average of two replications.

TABLE 26

Herbicidal Efficacy and Crop Tolerance of Compound 1 and Compound 2 in a Greenhouse Test

| TREATMENT | RATE GAI/HA[1] | % CONTROL OR INJURY[2] | | | | | |
|---|---|---|---|---|---|---|---|
| | | M101[3] | LEMONT[4] | CD[5] | AP[6] | AT[7] | SR[8] |
| Compound 1 | 1 | 0 | 10 | 60 | 0 | 80 | 90 |
| | 2 | 10 | 20 | 60 | 0 | 95 | 95 |
| | 4 | 10 | 40 | 80 | 60 | 95 | 95 |
| | 8 | 35 | 50 | 100 | 70 | 95 | 95 |
| Compound 2 | 1 | 0 | 30 | 70 | 0 | 95 | 0 |
| | 2 | 0 | 40 | 80 | 0 | 95 | 0 |
| | 4 | 30 | 70 | 100 | 20 | 95 | 80 |
| | 8 | 50 | 80 | 100 | 30 | 95 | 80 |
| Untreated | — | 0 | 0 | 0 | 0 | 0 | 0 |

[1]Application rate in grams active ingredient per hectare.
[2]Visual weed control or crop injury (relative to untreated check) on scale of:
0 to 100%
0 = no injury
100 = 100% plant death.
[3]M101 = japonica rice variety M101.
[4]LEMONT = indica rice variety Lemont.
[5]CD = *Cyperus difformis*
[6]AP = *Alternanthera philoxeroides*
[7]AT = *Alisma triviale*
[8]SR = *Sagittaria rigida*
[9]Rice was transplanted at the 2.0 to 2.5 leaf stage and treated 12 days later. Crop injury and weed control ratings were made 24 days after treatment.

TABLE 27

Expected[1] and Observed Activity of Combinations of Compound 1 and Benzsulfuron Methyl on Weeds

| Compound | Rate | Table/Species | Expected | Observed |
|---|---|---|---|---|
| 1 + Benzsulfuron Methyl | 2 + 10 | 10/SZ | 7.9 | 9.1 |
| | 2 + 10 | 10/CI | 2.0 | 6.33 |
| | 4 + 10 | 10/SZ | 9.3 | 9.93 |
| | 4 + 10 | 10/CI | 2.0 | 5.0 |
| | 4 + 20 | 10/SZ | 9.7 | 10 |
| | 4 + 20 | 10/CI | 8.0 | 9 |
| 1 + Benzsulfuron Methyl | 4 + 10 | 12/SZ | 8.4 | 10 |
| | 4 + 15 | 12/SZ | 8.8 | 10 |
| | 4 + 20 | 12/SZ | 8.4 | 10 |
| 1 + Benzsulfuron Methyl | 4 + 10 | 12/CI | 6.8 | 8.33 |
| | 4 + 15 | 12/CI | 9.0 | 10 |
| | 4 + 20 | 12/CI | 9.4 | 9.63 |
| 1 + Benzsulfuron Methyl | 4 + 15 | 12/JL | 9.46 | 10 |
| | 4 + 20 | 12/JL | 9.88 | 10 |
| 1 + Benzsulfuron Methyl | 4 + 15 | 13/CI | 9.83 | 10 |
| 1 + Benzsulfuron Methyl | 4 + 10 | 20/CI | 77 | 95 |
| | 4 + 10 | 20/FM | 80 | 100 |
| | 4 + 10 | 20/LL | 93.4 | 98 |
| | 4 + 10 | 20/SZ | 69.2 | 97 |
| 1 + Benzsulfuron Methyl | 4 + 15 | 20/CI | 90 | 100 |
| | 4 + 15 | 20/LL | 93.4 | 100 |
| | 4 + 15 | 20/SZ | 84 | 100 |
| 1 + Benzsulfuron Methyl | 4 + 20 | 20/CI | 95 | 98 |
| | 4 + 20 | 20/LL | 95.7 | 100 |
| | 4 + 20 | 20/SZ | 81.2 | 97 |
| 1 + Benzsulfuron Methyl | 2 + 25 | 24/EO | 1.9 | 4 |
| | 2 + 25 | 24/SJ | 8.5 | 9 |
| 1 + Benzsulfuron Methyl | 2 + 25 | 25/EO | 1.9 | 3 |
| | 2 + 25 | 25/SJ | 8.0 | 8.5 |
| | 2 + 25 | 25/CS | 2.0 | 3 |

[1]Kolby[2] equation for calculating synergism.

$$E = A + B - \frac{A \times B}{100}$$

E = expected value
A = observed value for Compound 1
B = observed value for benzsulfuron
if the observed value minus the expected value is positive, the combination is considered synergistic.
For example:
Table 20
A = 60 on SZ at 4 g/ha
B = 23 on SZ at 10 g/ha $$E = 60 + 23 - \frac{60 \times 23}{100}$$

E = 69.2
The observed value of Compound 1 in combination with benzsulfuron methyl on *sphenoclea zeylanica* at the 4 and 10 g rate respectively is 97.
Observed — Expected
97 − 69.2 = +27.8
[2]Kolby, S. R., Weeds 15:20-22, 1967.

TABLE 28

Expected and Observed Activity of Combinations of Compound 1 and Benzsulfuron Methyl on Rice

| Compound | Rate | Table Species | Expected | Observed |
|---|---|---|---|---|
| 1 + Benzsulfuron | 2 + 25 | 23/Va | 4.75 | 3.5 |

The expected injury to rice (as calculated by the Kolby equation) is reduced by the combination of Compound No. 1 with benzsulfuron methyl. This constitutes a substantial safening of the rice crop.

Selective herbicidal properties of mixtures of metsulfuron methyl and propanil are illustrated in the following greenhouse tests as Test B, C, D and E.

Test B

Seeds of barley (*Hordeum vulgare*), barnyardgrass (*Echinochloa crus-galli*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (*Digitaria spp.*), downy brome (*Bromus tectorum*), giant foxtail (*Setaria faberi*), green foxtail (*Setaria viridis*), jimsonweed (*Datura stramonium*), lambsquarters (*Chenopodium album*), morningglory (*Ipomoea spp.*), rape (*Brassica napus*), rice (*Oryza sativa*), sicklepod (*Cassia obtusifolia*), soybean (*Glycine max*), sugar beet (*Beta vulgaris*), teaweed (*Sida spinosa*), velvetleaf (*Abutilon theophrasti*), wheat (*Triticum aestivum*), wild buckwheat (*Polygonum convolvulus*), and wild oat (*Avena fatua*) and purple nutsedge (*Cyperus rotundus*) tubers were planted into a sandy loam soil with approximately one percent organic matter. These crop and weed species were allowed to grow to the two to three leaf stage (approximately two to eighteen cm) before the plants were treated postemergence with various ratios of mixtures of metsulfuron methyl and propanil. Both test chemicals were dissolved in a nonphytotoxic solvent before the compounds were applied to the plants. Treated plants and controls were maintained in a greenhouse for approximately twenty days, after which all species were compared to controls and visually evaluated. Plant response ratings, summarized in Table 29, are based on a scale of 0 to 100 where 0 is no effect and 100 is complete control. A dash (-) response means no test result. The ratio of Compound I to Compound II can be determined from the application rates of each compound as listed in the table.

TABLE 29

Plant Response

| | Compound I (alone) | | | |
|---|---|---|---|---|
| | Application Rate (g/ha) | | | |
| | 0.5 | 1 | 2 | 4 |
| Barley | 0 | 0 | 20 | 20 |
| Barnyardgrass | 0 | 0 | 20 | 60 |
| Blackgrass | 40 | 40 | 60 | 60 |
| Chickweed | 80 | 90 | 100 | 100 |
| Cocklebur | 20 | 20 | 30 | 70 |
| Corn | 20 | 30 | 30 | 50 |
| Cotton | 20 | 30 | 60 | 80 |
| Crabgrass | 0 | 0 | 0 | 30 |
| Downy brome | 0 | 0 | 0 | 0 |
| Giant foxtail | 0 | 0 | 0 | 0 |
| Green foxtail | 0 | 0 | 0 | 0 |
| Jimsonweed | 0 | 30 | 70 | 90 |
| Lambsquarters | 30 | 50 | 80 | 90 |
| Morningglory | 0 | 0 | 0 | 90 |
| Nutsedge | 0 | 0 | 0 | 0 |
| Rape | 0 | 60 | 90 | 100 |
| Rice | 20 | 0 | 0 | 40 |
| Sicklepod | 0 | 0 | 70 | 80 |
| Soybean | 20 | 50 | 70 | 80 |
| Sugar beet | 60 | 90 | 100 | 100 |
| Teaweed | 70 | 50 | 70 | 80 |
| Velvetleaf | 40 | 60 | 90 | 100 |
| Wheat | 0 | 0 | 0 | 0 |
| Wild buckwheat | 30 | 90 | 90 | 90 |
| Wild oat | 10 | 0 | 20 | 0 |

| Propanil at | Compound I (g/ha) | | | | |
|---|---|---|---|---|---|
| 250 g/ha | Zero | 0.5 | 1 | 2 | 4 |
| Barley | 0 | 0 | 0 | 0 | 20 |
| Barnyardgrass | 0 | 0 | 20 | 30 | 40 |
| Blackgrass | 0 | 0 | 30 | 50 | 50 |
| Chickweed | 0 | 90 | 90 | 100 | 100 |
| Cocklebur | 50 | 50 | 50 | 80 | 80 |
| Corn | 0 | 20 | 30 | 30 | 80 |
| Cotton | 60 | 60 | 60 | 70 | 80 |
| Crabgrass | 30 | 20 | 100 | 80 | 70 |
| Downy brome | 0 | 0 | 0 | 0 | 20 |
| Giant foxtail | 0 | 0 | 0 | 0 | 20 |
| Green foxtail | 0 | 0 | 0 | 20 | 30 |
| Jimsonweed | 0 | 70 | 70 | 70 | 90 |
| Lambsquarters | 50 | 70 | 100 | 100 | 100 |
| Morningglory | 30 | 70 | 70 | 90 | 90 |
| Nutsedge | 0 | 0 | 0 | 0 | — |
| Rape | 20 | 70 | 90 | 100 | 100 |
| Rice | 0 | 20 | 30 | 30 | 40 |
| Sicklepod | 30 | 60 | 50 | 70 | 70 |
| Soybean | 10 | 40 | 60 | 80 | 100 |
| Sugar beet | 30 | 80 | 80 | 100 | 100 |
| Teaweed | 0 | 20 | 40 | 80 | 90 |
| Velvetleaf | 80 | 80 | 90 | 100 | 100 |
| Wheat | 0 | 0 | 0 | 0 | 0 |
| Wild buckwheat | 0 | 30 | 80 | 90 | 90 |
| Wild oat | 0 | 0 | 10 | 10 | 30 |

| Propanil at | Compound I (g/ha) | | | | |
|---|---|---|---|---|---|
| 500 g/ha | Zero | 0.5 | 1 | 2 | 4 |
| Barley | 0 | 0 | 0 | 10 | 30 |
| Barnyardgrass | 20 | 30 | 40 | 60 | 70 |
| Blackgrass | 0 | 20 | 50 | 50 | 70 |
| Chickweed | 0 | 90 | 100 | 100 | 100 |
| Cocklebur | 40 | 70 | 70 | 60 | 80 |
| Corn | 0 | 20 | 40 | 40 | 80 |
| Cotton | 80 | 80 | 80 | 80 | 90 |
| Crabgrass | 50 | 20 | 20 | 100 | 100 |
| Downy brome | 0 | 0 | 0 | 0 | 20 |
| Giant foxtail | 0 | 0 | 20 | 30 | 0 |
| Green foxtail | 20 | 20 | 20 | 30 | 30 |
| Jimsonweed | 70 | 70 | 70 | 90 | 100 |
| Lambsquarters | 80 | 80 | 80 | 90 | 90 |
| Morningglory | 70 | 70 | 80 | 80 | 80 |
| Nutsedge | 0 | 0 | 0 | 0 | 0 |
| Rape | 60 | 90 | 90 | 100 | 100 |
| Rice | 0 | 20 | 10 | 30 | 40 |
| Sicklepod | 30 | 40 | 70 | — | 80 |
| Soybean | 30 | 70 | 70 | 100 | 100 |
| Sugar beet | 70 | 90 | 100 | 100 | 100 |
| Teaweed | 20 | 50 | 70 | 70 | 80 |
| Velvetleaf | 80 | 80 | 80 | 90 | 100 |
| Wheat | 0 | 0 | 0 | 0 | 0 |
| Wild buckwheat | 0 | 30 | 50 | 90 | 100 |
| Wild oat | 20 | 20 | 20 | 30 | 40 |

| Propanil at | Compound I (g/ha) | | | | |
|---|---|---|---|---|---|
| 1000 g/ha | Zero | 0.5 | 1 | 2 | 4 |
| Barley | 0 | 0 | 0 | 20 | 20 |
| Barnyardgrass | 30 | 40 | 60 | 30 | 40 |
| Blackgrass | 20 | 40 | 50 | 60 | 70 |
| Chickweed | 20 | 90 | 90 | 100 | 100 |
| Cocklebur | 30 | 70 | 70 | 70 | 70 |
| Corn | 0 | 30 | 30 | 60 | 80 |
| Cotton | 80 | 80 | — | 90 | 90 |
| Crabgrass | 50 | 80 | 80 | 40 | 50 |
| Downy brome | 0 | 20 | 0 | 0 | 0 |
| Giant foxtail | 40 | 0 | 0 | 20 | 40 |
| Green foxtail | 20 | 30 | 30 | 30 | 30 |
| Jimsonweed | 70 | 80 | 50 | 80 | 90 |
| Lambsquarters | 100 | 100 | 80 | 90 | 100 |
| Morningglory | 80 | 100 | 100 | 80 | 90 |
| Nutsedge | 0 | 0 | 0 | 0 | 0 |
| Rape | 90 | 100 | 100 | 100 | 100 |
| Rice | 70 | 20 | 20 | 40 | 50 |
| Sicklepod | 80 | 100 | 100 | 70 | 100 |
| Soybean | 20 | 40 | 50 | 100 | 100 |
| Sugar beet | 60 | 100 | 90 | 90 | 100 |
| Teaweed | 30 | — | 70 | 70 | 100 |
| Velvetleaf | 90 | 90 | 90 | 90 | 95 |
| Wheat | 0 | 0 | 0 | 0 | 0 |
| Wild buckwheat | 0 | 20 | 80 | 90 | 90 |
| Wild oat | 20 | 20 | 30 | 30 | 40 |

| Propanil at | Compound I (g/ha) | | | | |
|---|---|---|---|---|---|
| 2000 g/ha | Zero | 0.5 | 1 | 2 | 4 |
| Barley | 0 | 0 | 0 | 20 | 20 |
| Barnyardgrass | 60 | 90 | 80 | 80 | 70 |
| Blackgrass | 30 | 30 | 70 | 60 | 80 |
| Chickweed | 30 | 90 | 100 | 100 | 100 |
| Cocklebur | 80 | 80 | 80 | 80 | 80 |
| Corn | 20 | 20 | 20 | 50 | 70 |
| Cotton | 90 | 90 | 100 | 100 | 100 |
| Crabgrass | 100 | 100 | 100 | 100 | 100 |
| Downy brome | 30 | 30 | 30 | 30 | 30 |
| Giant foxtail | 50 | 70 | — | 80 | 60 |
| Green foxtail | 50 | 70 | 50 | 50 | 40 |
| Jimsonweed | 40 | 90 | 70 | 100 | 90 |

TABLE 29-continued

Plant Response

| | | | | | |
|---|---|---|---|---|---|
| Lambsquarters | 100 | 100 | 100 | 100 | 100 |
| Morningglory | 100 | 90 | 100 | 100 | 100 |
| Nutsedge | 0 | 0 | 0 | 0 | 0 |
| Rape | 100 | 100 | 100 | 100 | 100 |
| Rice | 30 | 40 | 50 | 50 | 60 |
| Sicklepod | 100 | 100 | 100 | 100 | 100 |
| Soybean | 30 | 80 | 80 | 90 | 90 |
| Sugar beet | 100 | 100 | 100 | 100 | 100 |
| Teaweed | 70 | — | 70 | 80 | 80 |
| Velvetleaf | 100 | 100 | 100 | 100 | 100 |
| Wheat | 20 | 20 | 20 | 20 | 20 |
| Wild buckwheat | — | 80 | 80 | 90 | 90 |
| Wild oat | 30 | 60 | 50 | 50 | 60 |

| Propanil at 4000 g/ha | Compound I (g/ha) | | | | |
|---|---|---|---|---|---|
| | Zero | 0.5 | 1 | 2 | 4 |
| Barley | 20 | 30 | 30 | 30 | 50 |
| Barnyardgrass | 80 | 90 | 100 | 90 | 100 |
| Blackgrass | 90 | 70 | 70 | 100 | 90 |
| Chickweed | 100 | 90 | 100 | 100 | 100 |
| Cocklebur | 30 | 30 | 90 | 90 | 80 |
| Corn | 30 | 30 | 30 | 50 | 80 |
| Cotton | 100 | 100 | 100 | 100 | 100 |
| Crabgrass | — | 100 | 100 | 100 | 100 |
| Downy brome | 30 | 70 | 70 | 70 | 70 |
| Giant foxtail | 30 | 100 | 80 | 100 | 70 |
| Green foxtail | 100 | — | 80 | 80 | 80 |
| Jimsonweed | 80 | 100 | 60 | 70 | 100 |
| Lambsquarters | 100 | 90 | 90 | 90 | 100 |
| Morningglory | 90 | 100 | 100 | 100 | 100 |
| Nutsedge | 0 | 0 | 0 | 0 | 0 |
| Rape | 100 | 100 | 100 | 100 | 100 |
| Rice | 30 | 60 | 60 | 70 | 60 |
| Sicklepod | 100 | 100 | 100 | 100 | 100 |
| Soybean | 80 | 70 | 90 | 80 | 90 |
| Sugar beet | 100 | 100 | 100 | 100 | 100 |
| Teaweed | 50 | 80 | 80 | 80 | 80 |
| Velvetleaf | 100 | 100 | — | 100 | 100 |
| Wheat | 25 | 25 | 25 | 25 | 25 |
| Wild buckwheat | 0 | 80 | 90 | 90 | 90 |
| Wild oat | 60 | 100 | 90 | 70 | 70 |

Test C

Seeds of barnyardgrass (*Echinochloa crus-galli*), cocklebur (*Xanthium pensylvanicum*), giant foxtail (*Setaria faberi*), hemp sesbania (*Sesbania exaltata*), morningglory (*Ipomoea spp.*), and Texas panicum (*Panicum taxanum*) were planted into a silt loam soil with approximately three percent organic matter. These weed species were allowed to grow to the two to three leaf stage (approximately eight to eighteen cm) before they were treated postemergence with mixtures of Compounds 1 and propanil dissolved in a non-phytotoxic solvent. Treated and untreated plants were placed in a greenhouse and visually evaluated for response injury approximately ten days after herbicide application. Each spray mixture of Compounds 1 and propanil was replicated three times. Response ratings, summarized in Table 30, are from 0 to 100 where 0 is no injury and 100 is plant death. The three letter code abbreviations listed in Table 30 have the following meanings:

REP = sample replication number
ECC = barnyardgrass (*Echinochloa crus-galli*)
IPH = ivy-leaf morningglory (*Ipomoea hederacea*)
PAT = Texas panicum (*Panicum texanum*)
SEE = Hemp sesbania (*Sesbania exaltata*)
SFA = Giant foxtail (*Setaria faberi*)
XAP = Cocklebur (*Xanthium pensylvanicum*)

TABLE 30

Weed Responses to Mixtures of Compound I with Propanil

| Propanil (g/ha) | Cmpd I (g/ha) | REP | ECC | IPH | PAT | SEE | SFA | XAP |
|---|---|---|---|---|---|---|---|---|
| 0 | 1 | 1 | 30 | 90 | 0 | 100 | 0 | 60 |
| 0 | 1 | 2 | 50 | 95 | 0 | 100 | 0 | 60 |
| 0 | 1 | 3 | 0 | 90 | 0 | 100 | 0 | 70 |
| 0 | 2 | 1 | 70 | 95 | 0 | 80 | 0 | 100 |
| 0 | 2 | 2 | 80 | 90 | 0 | 100 | 0 | 70 |
| 0 | 2 | 3 | 70 | 95 | 0 | 100 | 40 | 80 |
| 0 | 3 | 1 | 90 | 95 | 60 | 100 | 80 | 95 |
| 0 | 3 | 2 | 90 | 100 | 0 | 100 | 40 | 70 |
| 0 | 3 | 3 | 90 | 95 | 50 | 100 | 60 | 95 |
| 500 | 0 | 1 | 50 | 0 | 0 | 50 | 50 | 0 |
| 500 | 0 | 2 | 40 | 0 | 0 | 70 | 40 | 0 |
| 500 | 0 | 3 | 40 | 0 | 50 | 70 | 50 | 0 |
| 500 | 1 | 1 | 60 | 100 | 0 | 100 | 0 | 80 |
| 500 | 1 | 2 | 60 | 100 | 0 | 100 | 50 | 80 |
| 500 | 1 | 3 | 60 | 95 | 0 | 95 | 40 | 70 |
| 500 | 2 | 1 | 60 | 98 | 0 | 95 | 0 | 90 |
| 500 | 2 | 2 | 80 | 100 | 0 | 100 | 80 | 90 |
| 500 | 2 | 3 | 95 | 100 | 0 | 95 | 70 | 80 |
| 500 | 3 | 1 | 95 | 100 | 40 | 100 | 95 | 95 |
| 500 | 3 | 2 | 80 | 100 | 0 | 100 | 90 | 70 |
| 500 | 3 | 3 | 95 | 95 | 0 | 100 | 70 | 80 |
| 1000 | 0 | 1 | 70 | 0 | 50 | 100 | 80 | 50 |
| 1000 | 0 | 2 | 90 | 60 | 0 | 90 | 60 | 50 |
| 1000 | 0 | 3 | 60 | 40 | 50 | 60 | 60 | 40 |
| 1000 | 1 | 1 | 80 | 95 | 90 | 95 | 70 | 80 |
| 1000 | 1 | 2 | 95 | 100 | 0 | 100 | 70 | 90 |
| 1000 | 1 | 3 | 80 | 90 | 0 | 100 | 80 | 80 |
| 1000 | 2 | 1 | 95 | 98 | 0 | 98 | 70 | 95 |
| 1000 | 2 | 2 | 95 | 100 | 0 | 95 | 80 | 95 |
| 1000 | 2 | 3 | 95 | 95 | 0 | 95 | 80 | 90 |
| 1000 | 3 | 1 | 98 | 100 | 40 | 100 | 80 | 95 |
| 1000 | 3 | 2 | 90 | 95 | 40 | 95 | 90 | 80 |
| 1000 | 3 | 3 | 95 | 100 | 50 | 100 | 90 | 95 |
| 2000 | 0 | 1 | 80 | 80 | 50 | 100 | 100 | 50 |
| 2000 | 0 | 2 | 100 | 70 | 60 | 100 | 90 | 80 |
| 2000 | 0 | 3 | 100 | 80 | 90 | 100 | 100 | 80 |
| 2000 | 1 | 1 | 90 | 95 | 100 | 100 | 95 | 100 |
| 2000 | 1 | 2 | 98 | 95 | 90 | 100 | 100 | 100 |
| 2000 | 1 | 3 | 95 | 95 | 40 | 100 | 95 | 90 |
| 2000 | 2 | 1 | 98 | 98 | 80 | 100 | 100 | 95 |
| 2000 | 2 | 2 | 100 | 100 | 60 | 100 | 95 | 95 |
| 2000 | 2 | 3 | 95 | 95 | 50 | 100 | 100 | 95 |
| 2000 | 3 | 1 | 100 | 98 | 70 | 100 | 100 | 95 |
| 2000 | 3 | 2 | 95 | 100 | 100 | 100 | 100 | 95 |
| 2000 | 3 | 3 | 100 | 100 | 40 | 100 | 100 | 100 |

Test D

The synergistic activity of mixtures of Compound I and propanil on yellow nutsedge (*Cyperus esculentus*) is illustrated in this test. Experimental test methods and results, methods of data analysis, and observed and predicted test results based upon Colby's equation to determine synergism are presented in the following information.

Tubers of yellow nutsedge were planted in 10-cm diameter plastic pots filled with eight cm of pasteurized silt loam soil with approximately three percent organic matter. The tubers were allowed to germinate and grow for one week before the plants were thinned to 5 uniform plants per pot. At two weeks after planting when the nutsedge was approximately 25 cm tall, the pots were treated postemergence with the indicated mixtures of Compounds I and propanil dissolved in a non-phytotoxic solvent. Each treatment was replicated three times. Treated and untreated plants were placed in a greenhouse. At three days after treatment, the pots were flooded with 5 cm of water to simulate a paddy environment. Approximately 2 weeks after treatment, fresh weights of the aerial portions of plants for each treatment were taken. Fresh weight responses are summarized in Table 31.

TABLE 31

Nutsedge response to mixtures of Compound I with Propanil

| Propanil (g/ha) | CMPD I (g/ha) | Nutsedge fresh wt in grams | | |
|---|---|---|---|---|
| | | REP 1 | REP 2 | REP 3 |
| 0 | 0 | 47.78 | 49.41 | 46.45 |
| 1000 | 0 | 42.70 | 35.73 | 42.35 |
| 2000 | 0 | 40.00 | 39.89 | 37.81 |
| 3000 | 0 | 27.97 | 28.48 | 28.77 |
| 4000 | 0 | 22.24 | 17.61 | 22.15 |
| 0 | 1 | 42.09 | 41.24 | 41.58 |
| 1000 | 1 | 25.48 | 19.47 | 27.76 |
| 2000 | 1 | 24.56 | 29.70 | 29.58 |
| 3000 | 1 | 26.51 | 29.42 | 23.75 |
| 4000 | 1 | 17.91 | 17.70 | 23.50 |
| 0 | 2 | 32.90 | 39.95 | 31.10 |
| 1000 | 2 | 30.91 | 24.68 | 24.31 |
| 2000 | 2 | 27.68 | 18.87 | 20.57 |
| 3000 | 2 | 23.11 | 25.08 | 24.82 |
| 4000 | 2 | 14.43 | 14.12 | 24.45 |
| 0 | 4 | 28.55 | 31.95 | 28.13 |
| 1000 | 4 | 23.86 | 27.58 | 29.58 |
| 2000 | 4 | 25.01 | 17.05 | 23.44 |
| 3000 | 4 | 21.96 | 21.10 | 12.24 |
| 4000 | 4 | 15.95 | 12.14 | 18.00 |
| 0 | 6 | 37.05 | 25.30 | 32.44 |
| 1000 | 6 | 23.95 | 26.78 | 27.79 |
| 2000 | 6 | 19.73 | 26.21 | 20.42 |
| 3000 | 6 | 20.22 | 16.14 | 16.19 |
| 4000 | 6 | 19.85 | 10.42 | 10.77 |
| 0 | 8 | 24.69 | 27.32 | 24.98 |
| 1000 | 8 | 29.28 | 25.44 | 24.62 |
| 2000 | 8 | 20.17 | 12.95 | 23.40 |
| 3000 | 8 | 14.80 | 14.84 | 22.27 |
| 4000 | 8 | 18.77 | 19.81 | 25.69 |

Means of the three replicates for each set of treatments were converted to percent control using the formula:

$$\% \text{ control} = \left(1 - \frac{\text{fresh weight of aerial part of treated nutsedge}}{\text{fresh weight of aerial part of untreated nutsedge}}\right) \times 100.$$

Expected plant responses were calculated with Colby's equation (see Colby, S. R. Calculating synergistic and Antagonistic Responses of Herbicide combinations. Weeds 15:20–22, 1967) which is:

$$E = (CI + CII) - \left(\frac{CI \times CII}{100}\right)$$

where:
CI = the percent inhibition of growth by Compound I at treatment rate A g/ha.
CII = the percent inhibition of growth by Compound II at treatment rate B g/ha.
E = the expected percent inhibition of growth by Compound I plus Compound II at treatment rate A plus B g/ha.

Thus when the observed response is greater than expected, the combination is synergistic. The synergistic response of mixtures of Compounds I and propanil on nutsedge is demonstrated in Table 32.

TABLE 32

Herbicidal Effects of Mixtures of Compound I and Propanil

| Propanil (g/ha) | CMPD I (g/ha) | Mean Fresh Weight | % Control (Actual Observed) | % Control (Expected Colby) |
|---|---|---|---|---|
| 0 | 0 | 47.88 | 0 | — |
| 0 | 1 | 41.64 | 13 | — |
| 0 | 2 | 34.65 | 28 | — |
| 0 | 4 | 29.54 | 38 | — |
| 0 | 6 | 31.60 | 34 | — |
| 0 | 8 | 25.66 | 46 | — |
| 1000 | 0 | 40.26 | 16 | — |
| 1000 | 1 | 24.24 | 49 | 27 |
| 1000 | 2 | 26.63 | 44 | 39 |
| 1000 | 4 | 27.01 | 44 | 48 |
| 1000 | 6 | 26.17 | 45 | 45 |
| 1000 | 8 | 26.45 | 45 | 55 |
| 2000 | 0 | 39.23 | 18 | — |
| 2000 | 1 | 27.95 | 42 | 29 |
| 2000 | 2 | 22.37 | 53 | 41 |
| 2000 | 4 | 21.83 | 54 | 49 |
| 2000 | 6 | 22.12 | 54 | 46 |
| 2000 | 8 | 18.84 | 61 | 56 |
| 3000 | 0 | 28.41 | 41 | — |
| 3000 | 1 | 26.56 | 45 | 48 |
| 3000 | 2 | 24.34 | 49 | 57 |
| 3000 | 4 | 18.43 | 62 | 63 |
| 3000 | 6 | 17.52 | 63 | 61 |
| 3000 | 8 | 17.30 | 64 | 68 |
| 4000 | 0 | 20.67 | 57 | — |
| 4000 | 1 | 19.70 | 59 | 62 |
| 4000 | 2 | 17.67 | 63 | 69 |
| 4000 | 4 | 15.36 | 68 | 73 |
| 4000 | 6 | 13.68 | 71 | 72 |
| 4000 | 8 | 21.42 | 55 | 77 |

Test E

The synergistic activity of mixtures of Compound I and propanil on *Echinochloa crus-gali* (barnyardgrass) and especially *Fimbristylis* (sedge) is further illustrated in this test, conducted on field trials in the Dominican Republic.

Mixtures of Compound I and propanil were applied as a spray directly to the seedlings 18–21 days after seeding. Paddy fields are drained 1–2 days prior to application and flooded again the next day of application. The results are tabulated below in Table 33.

TABLE 33

| Test Results Compound Sedge | Use Rate g ai/ha | Phyto. (%) | Weed Control (%) | | |
|---|---|---|---|---|---|
| | | | Ec | Bl | |
| I and Propanil | 6 + 3400 | 0 | 95 | 100 | 100 |
| I and Propanil | 4.8 + 3400 | 0 | 95 | 100 | 100 |
| 1,4-D + Propanil | 72 + 3400 | 0 | 90 | 60 | 50 |
| I | 6 | 0 | 0 | 100 | 0 |
| I | 4.8 | 0 | 0 | 100 | 0 |
| Propanil | 3400 | 0 | 90 | 10 | 10 |

Ec: *Echinochloa crus-gali*
Bl: *Heteranthera limosa, Ludwigia* spp.
Sedge: *Fimbristylis* spp.

What is claimed is:
1. A method for controlling the growth of undesired vegetation in a rice crop by applying to the crop after transplantation or emergence an effective amount of a compound of Formula I

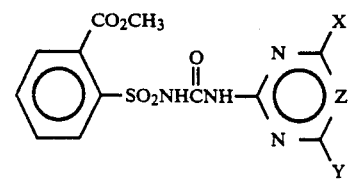

wherein
X is $CH_3$;
Y is $OCH_3$; and
Z is N.

* * * * *